(12) United States Patent
Takekawa et al.

(10) Patent No.: US 7,645,607 B2
(45) Date of Patent: Jan. 12, 2010

(54) METHOD FOR PRODUCING OPTICALLY ACTIVE N-PROTECTED-PROPARGYLGLYCINE

(75) Inventors: Yuki Takekawa, Amagasaki (JP); Isao Kurimoto, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 312 days.

(21) Appl. No.: 11/378,366

(22) Filed: Mar. 20, 2006

(65) Prior Publication Data
US 2006/0216806 A1    Sep. 28, 2006

(30) Foreign Application Priority Data
Mar. 22, 2005    (JP)    ............................. 2005-081364

(51) Int. Cl.
C12P 41/00    (2006.01)
(52) U.S. Cl. .................. 435/280; 435/106; 435/325; 435/195
(58) Field of Classification Search ................. 435/280, 435/106
See application file for complete search history.

(56) References Cited

U.S. PATENT DOCUMENTS 5,665,598 A * 9/1997 Abood et al. ............... 435/280

FOREIGN PATENT DOCUMENTS

WO    WO 95/28385 A1    10/1995

OTHER PUBLICATIONS

Retrieved Nov. 30, 2008, from http://www.merriam-webster.com/dictionary/derive.*
Xu et al., "Novozym-435-catalyzed enzymatic separation of racemic propargylic alcohols. A facile route to optically active terminal aryl propargylic alcohols", Tetrahedron Letters, 2003, 6343-6346, vol. 44.
Chenault et al., "Kinetic resolution of unnatural and rarely occurring amino acids: Enantioselective hydrolysis of N-acyl animo acids catalyzed by acylase I", J. Amer. Chem. Soc., 1989, 6354-6364, vol. 111.
Larissa B. Wolf et al.; A Biocatalytic Route to Enantiomerically Pure Unsaturated α-H-α-Amino Acids, Adv. Synth. Catal. 2001, 343, No. 6-7; Wiley-VCH Verlag GmbH, 69451 Weinheim, Germany, 2001, pp. 662-674.
Othmar Leukart et al.; 224. Synthesis of L-Propargylglycine and Derivatives[1]), Helvetica Chimica Acta-vol. 59, Fasc. 6 (1976)—Nr. 224; pp. 2181-2183, T=Institut für Molekularbiològie und Biophysik Eidgenössische Technishe Hochschule, CH-8093 Zürich.
Anna Lopez et al.; Highly diastereoselective monoalkylation and Michael addition of N-(diphenylmethylene) glycinesultam under solid-liquid phase-transfer catalysis conditions using potassium carbonate as base, Tetrahedron: Asymmetry 9 (1998) 1967-1977, Department of Chemistry; Universitat Autonama de Barcelona, Bellaterra, 08193 Barcelona, Spain.
Sylvain Collet et al.; Stereoselective, nonracemic synthesis of ω-borono-α-amino acids, Synthese et electrosynthese organiques, UMR 6510, Universite de Rennes 1, 35042 Rennes Cedex, France; Tetrahedron: Asymmetry 9 (1998) 2121-2131.
Kiyoshi Tanaka et al., Asymmetric Synthesis of Uncommon α-Amino Acids by Diastereoselective Alkylations of a Chiral Glycine Equivalent, RIL: S0957-4166(96)00212-1, Tetrahedron: Asymmetry, vol. 7, No. 6, pp. 1771-1782, 1996, Institute for Chemical Research, Kyoto University, Uji, Kyoto 611, Japan. 1996 Elsevier Science Ltd, printed in Great Britain.
Satoru Ikegami et al., Asymmetric Synthesis of α-Amino Acids by Alkylation of N-[N-BIS-(Methylthio) Methylenieglycyl]-2,5-Bis(Methoxymethoxymethyl)PyrrolidineAnd Enantioselective Synthesis of Protected (2S,9S)-2-Amino-8-Oxo-9,10-Epoxydecaniuc Acid, Department of Chemistry, Faculty of Science, Kyushu University 33, Hakozaki, Higashi-ku, Fukuoka 312, Japan, Tetrahedron vol. 44, No. 17, pp. 5333 to 5342, 1988, printed in Great Britain.

* cited by examiner

Primary Examiner—Sandra Saucier
Assistant Examiner—Susan Hanley
(74) Attorney, Agent, or Firm—Sughrue Mion, PLLC

(57) ABSTRACT

A method for producing (S)—N-protected-propargylglycine of the following formula (2), wherein the method comprises asymmetrically hydrolyzing an N-protected-propargylglycine ester of the following formula (1) by using an asymmetric hydrolysis enzyme or a cultured substance of a microorganism having an ability of producing this enzyme or a treated substance thereof.

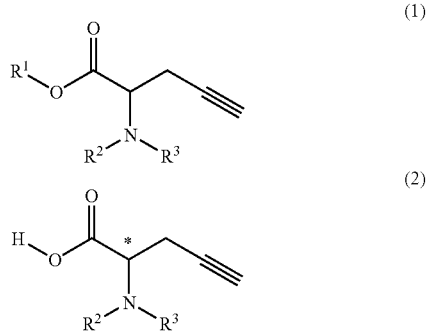

The hydrolysis enzyme is obtained from a microorganism selected from the group consisting of *Thermomyces* genus, *Aspergillus* genus, *Rhizopus* genus, *Penicillium* genus, *Pseudomonas* genus, *Humicola* genus, *Burkholderia* genus, *Candida* genus *Bacillus* genus and *Streptomyces* genus.

16 Claims, No Drawings

METHOD FOR PRODUCING OPTICALLY ACTIVE N-PROTECTED-PROPARGYLGLYCINE

TECHNICAL FIELD OF THE INVENTION

The present invention relates to a method for producing optically active N-protected-propargylglycine.

BACKGROUND OF THE INVENTION

Japanese Patent Application National Publication (Laid-Open) No. 9-512012, p. 20 to 22 discloses that asymmetric hydrolysis of methyl
2-[{(1,1-dimethylethoxy)carbonyl}amino]-4-pentynoate using α-chymotrypsin in a phosphate buffer and the subsequent post treatment thereof give
2-(S)-[{(1,1-dimethylethoxy)carbonyl}amino]-4-pentynoic acid having an enantiomer excess of 88% e.e. and discloses that processes of dissolving the resultant
2-(S)-[{(1,1-dimethylethoxy)carbonyl}amino]-4-pentynoic acid in an ether-based solvent and crystallizing this from the solvent give
2-(S)-[{(1,1-dimethylethoxy)carbonyl}amino]-4-pentynoic acid having an enantiomer excess of 99% e.e. Thus, the method described in Laid-Open No. 9-512012 needs further a process of recrystallization for obtaining an intended compound having high optical purity.

The present inventors have investigated to find a method for producing optically active N-protected-propargylglycine with few problems as described above and resultantly found that an intended compound of high optical purity needing no recrystallization process can be produced by using an enzyme derived from a certain kind of microorganism.

DISCLOSURE OF THE INVENTION

The present invention is to provide a method for producing (S)-N-protected-propargylglycine having high optical purity.

That is, the present invention provides the following [1] to [15].

[1] A Method for Producing (S)-N-protected-propargylglycine of the following formula (2), wherein the method comprises asymmetrically hydrolyzing an N-protected-propargylglycine ester of the following formula (1) by using the following asymmetric hydrolysis enzyme or a cultured substance of a microorganism having an ability of producing this enzyme or a treated substance thereof.

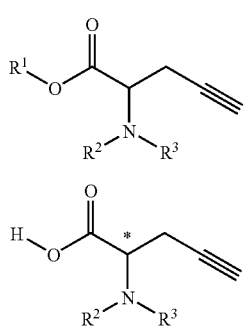

(wherein, $R^1$ represents an alkyl group having 1 to 4 carbon atoms, $R^2$ and $R^3$ each independently represent a hydrogen atom or a protective group of an amino group, $R^2$ and $R^3$ being not simultaneously a hydrogen atom, and a carbon atom appended with a mark * represents an asymmetric carbon atom.).

[Asymmetric Hydrolysis Enzyme]

Hydrolysis enzymes derived from a microorganism selected from the group consisting of *Thermomyces* genus, *Aspergillus* genus, *Rhizopus* genus, *Penicillium* genus, *Pseudomonas* genus, *Humicola* genus, *Burkholderia* genus, *Candida* genus and *Streptomyces* genus. [2] The method according to [1], wherein $R^2$ represents a protective group of an amino group, this protective group is a protective group of the formula $R^4$—O—Co— (wherein, $R^4$ represents an alkyl group, aralkyl group or aryl group) or a protective group of the formula $R^7$—$CH_2$— (wherein, $R^7$ represents an aryl group), and $R^3$ represents a hydrogen atom.

[3] The method according to [1] or [2], wherein $R^2$ represents a tert-butoxycarbonyl group and $R^3$ represents a hydrogen atom.

[4] The method according to any one of [1] to [3], wherein $R^1$ represents an ethyl group.

[5] The method according to any one of [1] to [4], wherein the asymmetric hydrolysis enzyme is a hydrolysis enzyme derived from the following microorganism.

[Microorganism]

Hydrolysis enzymes derived from a microorganism selected from the group consisting of *Thermomyces* genus, *Aspergillus niger, Rhizopus* genus, *Aspergillus oryzae, Penicillium* genus, *Pseudomonas* genus, *Humicola* genus, *Aspergillus melleus* (acylase), *Burkholderia* genus and *Streptomyces* genus.

[6] The method according to any one of [1] to [5], wherein the asymmetric hydrolysis enzyme is a hydrolysis enzyme derived from the following microorganism.

[Microorganism]

A microorganism selected from the group consisting of *Thermomyces lanuginosa, Aspergillus niger, Rhizopus niveus, Aspergillus oryzae, Penicillium citrinum, Pseudomonas* sp., *Humicola* sp., *Aspergillus melleus* (acylase), *Burkholderia cepacia* and *Streptomyces caespitosus*.

[7] The production method according to any one of [1] to [6], wherein the asymmetric hydrolysis enzyme is α-amylase derived form a microorganism selected from the group consisting of *Bacillus subtilis* and *Bacillus licheniformis*.

[8] A method for producing (R)-N-protected-propargylglycine wherein a (S)-N-protected-propargylglycine ester in an N-protected-propargylglycine ester of the following formula (1) is asymmetrically hydrolyzed by using the following asymmetric hydrolysis enzyme or a cultured substance of a microorganism having an ability of producing this enzyme or a treated substance thereof, then, (S)-N-protected-propargylglycine is separated, and an unreacted (R)-N-protected-propargylglycine ester is hydrolyzed.

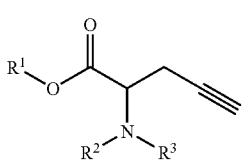

(1)

(wherein, $R^1$ represents an alkyl group having 1 to 4 carbon atoms, $R^2$ and $R^3$ each independently represent a hydrogen atom or a protective group of an amino group, $R^2$ and $R^3$ being not simultaneously a hydrogen atom, and a carbon atom appended with a mark * represents an asymmetric carbon atom.).

[Asymmetric Hydrolysis Enzyme]

Hydrolysis enzymes derived from a microorganism selected from the group consisting of *Thermomyces* genus, *Aspergillus* genus, *Rhizopus* genus, *Penicillium* genus, *Pseudomonas* genus, *Humicola* genus, *Burkholderia* genus, *Candida* genus and *Streptomyces* genus.

[9] The method according to [8], wherein $R^2$ represents a protective group of an amino group, this protective group is a protective group of the formula $R^4$—O—Co— (wherein, $R^4$ represents an alkyl group, aralkyl group or aryl group) or a protective group of the formula $R^7$—$CH_2$— {wherein, $R^7$ represents an aryl group}, and $R^3$ represents a hydrogen atom.

[10] The method according to [8] or [9], wherein $R^2$ represents a tert-butoxycarbonyl group and $R^3$ represents a hydrogen atom.

[11] The method according to any one of [8] to [10], wherein $R^1$ represents an ethyl group.

[12] The method according to any one of [8] to [11], wherein the asymmetric hydrolysis enzyme is a hydrolysis enzyme derived from the following microorganism.

[Microorganism]

A microorganism selected from the group consisting of *Thermomyces* genus, *Aspergillus oryzae*, *Penicillium* genus, *Aspergillus melleus*, *Rhizopus niveus* (protease), *Humicola* sp., *Candida* genus and *Streptomyces* genus.

[13] The production method according to any one of [8] to [12], wherein the asymmetric hydrolysis enzyme is a hydrolysis enzyme derived from the following microorganism.

[Microorganism]

A microorganism selected from the group consisting of *Thermomyces lanuginosa*, *Aspergillus oryzae*, *Penicillium citrinum*, *Aspergillus melleus*, *Rhizopus niveus* (protease), *Humicola* sp., *Candida antactica* and *Streptomyces caespitosus*.

[14] The method according to any one of [8] to [13], wherein the asymmetric hydrolysis enzyme is α-amylase derived form a microorganism selected from the group consisting of *Bacillus subtilis* and *Bacillus licheniformis*.

[15] A method for producing
(R)-N-protected-propargylglycine wherein a
(S)-N-protected-propargylglycine ester in an N-protected-propargylglycine ester of the following formula (1) is asymmetrically hydrolyzed by using an esterase derived from a thermophilic microorganism.

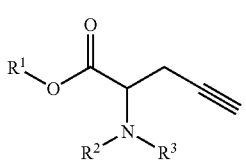

(1)

(wherein, $R^1$ represents an alkyl group having 1 to 4 carbon atoms, $R^2$ and $R^3$ each independently represent a hydrogen atom or a protective group of an amino group, $R^2$ and $R^3$ being not simultaneously a hydrogen atom, and a carbon atom appended with a mark * represents an asymmetric carbon atom)

MODES FOR CARRYING OUT THE INVENTION

The present invention will be illustrated in detail below.

In the present invention, the N-protected-propargylglycine ester (1) (hereinafter, referred to as substrate in some cases) can be produced, for example, according to a method described in Tetrahedron Letters, 40, 5841-5844 (1999) in which a glycine ester hydrochloride is converted into a Schiff base before alkylation, then, the resultant imine compound is hydrolyzed, and an amino group in the resultant propargylglycine ester is protected by an ordinary method. The substrate in the present invention can also be produced according to a method described in Helvetica Chimica Acta, 59(6), 2181-2183, (1976) in which an N-protected-α-aminomalonic acid diester is alkylated with propargyl bromide, then, hydrolyzed according to an ordinary method, subsequently, subjected to a decarboxylation reaction.

The above-mentioned substrate may be that which has been produced by other methods than the above-mentioned methods. In the present invention, the above-mentioned substrate is present in the form of a mixture of two kinds of enantiomers (racemate).

In the above-mentioned substrate, $R^1$ represents an alkyl group having 1 to 4 carbon atoms. Examples of the above-mentioned alkyl group include a methyl group, ethyl group, n-propyl group, isopropyl group, n-butyl group, isobutyl group, sec-butyl group, tert-butyl group and the like, and preferable is an ethyl group.

In the above-mentioned substrate, $R^2$ and $R^3$ represent a hydrogen atom or a protective group of an amino group, but $R^2$ and $R^3$ are not simultaneously a hydrogen atom.

As the above-mentioned protective group of an amino group, for example, the following groups are mentioned.

Protective groups of the formula $R^4$—OCO— {wherein, $R^4$ represents an alkyl group, aralkyl group or aryl group} and protective groups of the formula $R^7$—$CH_2$— {wherein, $R^7$ represents an aryl group}.

Here, the alkyl group includes alkyl groups having 1 to 6 carbon atoms, and specific examples thereof include a methyl group, ethyl group, n-propyl group, iso-propyl group, n-butyl group, sec-butyl group, tert-butyl group and the like. The aralkyl group include aralkyl groups having 7 to 12 carbon atoms, and specific examples thereof include a benzyl group, p-methoxybenzyl group, p-nitrobenzyl group and the like. The aryl group includes aryl groups having 5 to 12 carbon atoms, and specific examples thereof include a phenyl group, naphthyl group, biphenyl group, p-methylphenyl group, pyridyl group and the like.

Specific examples of the above-mentioned protective group include alkoxycarbonyl groups such as a tert-butoxycarbonyl group; arylalkyloxycarbonyl groups such as a benzyloxycarbonyl group, p-methoxybenzyloxycarbonyl group and p-nitrobenzyloxycarbonyl group; allyloxy or alkoxycarbonyl groups such as an allyloxycarbonyl group and 9-fluorenylmethoxycarbonyl group; acyl groups such as an acetyl group and benzoyl group; substituted alkyl groups such as a benzyl group, and the like.

Among them, a tert-butoxycarbonyl group, benzyloxycarbonyl group, benzoyl group and benzyl group are preferable as the protective group of an amino group.

Specific examples of the above-mentioned substrate include
N-tert-butoxycarbonyl-propargylglycine methyl ester,
N-benzyloxycarbonyl-propargylglycine methyl ester,
N-p-methoxybenzyloxycarbonyl-propargylglycine methyl ester,
N-p-nitrobenzyloxycarbonyl-propargylglycine methyl ester,
N-allyloxycarbonyl-propargylglycine methyl ester,
N-9-fluorenylmethoxycarbonyl-propargylglycine methyl ester,
N-acetyl-propargylglycine methyl ester,
N-benzyl-propargylglycine methyl ester,
N-tert-butoxycarbonyl-propargylglycine ethyl ester,
N-benzyloxycarbonyl-propargylglycine ethyl ester,
N-p-methoxybenzyloxycarbonyl-propargylglycine ethyl ester,
N-p-nitrobenzyloxycarbonyl-propargylglycine ethyl ester,
N-allyloxycarbonyl-propargylglycine ethyl ester,
N-9-fluorenylmethoxycarbonyl-propargylglycine ethyl ester,
N-acetyl-propargylglycine ethyl ester,
N-benzyl-propargylglycine ethyl ester,
N-tert-butoxycarbonyl-propargylglycine-n-propyl ester,
N-benzyloxycarbonyl-propargylglycine-n-propyl ester,
N-p-methoxybenzyloxycarbonyl-propargylglycine-n-propyl ester, N-p-nitrobenzyloxycarbonyl-propargylglycine-n-propyl ester, N-allyloxycarbonyl-propargylglycine-n-propyl ester,
N-9-fluorenylmethoxycarbonyl-propargylglycine-n-propyl ester, N-acetyl-propargylglycine-n-propyl ester,
N-benzyl-propargylglycine-n-propyl ester,
N-tert-butoxycarbonyl-propargylglycine isopropyl ester,
N-benzyloxycarbonyl-propargylglycine isopropyl ester,
N-p-methoxybenzyloxycarbonyl-propargylglycine isopropyl ester, N-p-nitrobenzyloxycarbonyl-propargylglycine isopropyl ester, N-allyloxycarbonyl-propargylglycine isopropyl ester,
N-9-fluorenylmethoxycarbonyl-propargylglycine isopropyl ester, N-acetyl-propargylglycine isopropyl ester,
N-benzyl-propargylglycine isopropyl ester,
N-tert-butoxycarbonyl-propargylglycine-n-butyl ester,
N-benzyloxycarbonyl-propargylglycine-n-butyl ester,
N-p-methoxybenzyloxycarbonyl-propargylglycine-n-butyl ester,
N-p-nitrobenzyloxycarbonyl-propargylglycine-n-butyl ester,
N-allyloxycarbonyl-propargylglycine-n-butyl ester,
N-9-fluorenylmethoxycarbonyl-propargylglycine-n-butyl ester,
N-acetyl-propargylglycine-n-butyl ester,
N-benzyl-propargylglycine-n-butyl ester,
N-tert-butoxycarbonyl-propargylglycine isobutyl ester,
N-benzyloxycarbonyl-propargylglycine isobutyl ester,
N-p-methoxybenzyloxycarbonyl-propargylglycine isobutyl ester,
N-p-nitrobenzyloxycarbonyl-propargylglycine isobutyl ester,
N-allyloxycarbonyl-propargylglycine isobutyl ester,
N-9-fluorenylmethoxycarbonyl-propargylglycine isobutyl ester,
N-acetyl-propargylglycine isobutyl ester,
N-benzyl-propargylglycine isobutyl ester,
N-tert-butoxycarbonyl-propargylglycine-sec-butyl ester,
N-benzyloxycarbonyl-propargylglycine-sec-butyl ester,
N-p-methoxybenzyloxycarbonyl-propargylglycine-sec-butyl ester,
N-p-nitrobenzyloxycarbonyl-propargylglycine-sec-butyl ester,
N-allyloxycarbonyl-propargylglycine-sec-butyl ester,
N-9-fluorenylmethoxycarbonyl-propargylglycine-sec-butyl ester, N-acetyl-propargylglycine-sec-butyl ester,
N-benzyl-propargylglycine-sec-butyl ester,
N-tert-butoxycarbonyl-propargylglycine-tert-butyl ester,
N-benzyloxycarbonyl-propargylglycine-tert-butyl ester,
N-p-methoxybenzyloxycarbonyl-propargylglycine-tert-butyl ester,
N-p-nitrobenzyloxycarbonyl-propargylglycine-tert-butyl ester, N-allyloxycarbonyl-propargylglycine-tert-butyl ester,
N-9-fluorenylmethoxycarbonyl-propargylglycine-tert-butyl ester, N-acetyl-propargylglycine-tert-butyl ester,
N-benzyl-propargylglycine-tert-butyl ester, and the like.

As the enzyme for producing optically active N-protected-propargylglycine which has an ability of asymmetrical hydrolysis for the above-mentioned substrate, for example, hydrolysis enzymes derived from microorganisms of *Thermomyces* genus, *Aspergillus* genus, *Rhizopus* genus, *Penicillium* genus, *Pseudomonas* genus, *Humicola* genus, *Burkholderia* genus, *Candida* genus and *Streptomyces* genus, and the like are mentioned.

As the above-mentioned hydrolysis enzyme derived from a microorganism of *Thermomyces* genus, for example, enzymes derived from *Thermomyces lanuginosa* (esterase, protease or lipase) are mentioned.

As the above-mentioned hydrolysis enzyme derived from a microorganism of *Aspergillus* genus, for example, enzymes derived from *Aspergillus niger, Aspergillus oryzae, Asgergillus melleus* (esterase, protease, acylase or lipase) are mentioned.

As the above-mentioned hydrolysis enzyme derived from a microorganism of *Rhizopus* genus, for example, enzymes derived from *Rhizopus niveus* (esterase, protease or lipase) are mentioned.

As the above-mentioned hydrolysis enzyme derived from a microorganism of *Penicillium* genus, for example, enzymes derived from *Penicillium citrinum* (esterase, protease or lipase) are mentioned.

As the above-mentioned hydrolysis enzyme derived from a microorganism of *Pseudomonas* genus, esterase, protease, lipase and the like are mentioned.

As the above-mentioned hydrolysis enzyme derived from a microorganism of *Burkholderia* genus, for example, enzymes derived from *Burkholderia cepacia* (esterase, protease or lipase) are mentioned.

As the above-mentioned hydrolysis enzyme derived from a microorganism of *Candida* genus, for example, enzymes derived from *Candida antactica* (esterase, protease or lipase) are mentioned.

As the above-mentioned hydrolysis enzyme derived from a microorganism of *Streptomyces* genus, for example, enzymes derived from *Streptomyces caespitosus* (esterase, protease or lipase) are mentioned.

As the enzyme for producing optically active N-protected-propargylglycine which has an ability of asymmetrical hydrolysis for the above-mentioned substrate, for example, α-amylase derived from *Bacillus subtilis* and *Bacillus licheniformis*, and a commercially available enzyme CHIRAZYME E-3, lyo (manufactured by Roche Diagnostics) which is an esterase derived from a thermophilic microorganism, are mentioned.

As the enzyme for producing optically active N-protected-propargylglycine having an ability of asymmetrical hydrolysis for the above-mentioned substrate, the following enzymes are specifically listed.

[Commercially Available Enzymes Manufactured by Amamo Enzyme]

Lipase CE "AMANO" 5 (derived from *Thermomyces lanuginosa*); Lipase N "AMANO", Newlase F (derived from *Rhizopus niveus*); Lipase A "AMANO" 6 (derived from *Aspergillus niger*); Lipase CE (derived from *Humicola* sp.); Protease A "AMANO", Protease M "AMANO" (derived from *Aspergillus oryzae*); Protease B "AMANO" (derived from *Penicillium citrinum*); Protease P "AMANO", acylase (derived from *Aspergillus melleus*); CHE "AMANO" 2 (derived from *Pseudomonas* sp.)

[Commercially Available Enzymes Manufactured by Roche Diagnostics]

CHIRAZYME L-1, lyo (derived from *Burkholderia cepacia*); CHIRAZYME L-6, lyo (derived from *Pseudomonas* sp.), CHIRAZYME L-2, c-f., C2, lyo (derived from *Candida antactica*)

[Commercially Available Enzymes Manufactured by Novozyme]

Termamyl (derived from *Bacillus licheniformis*), BAN (derived from *Bacillus subtilis*)

As the enzyme giving (S)-N-protected-propargylglycine with an enantiomer excess of over 88% e.e., there are mentioned hydrolysis enzymes derived from a microorganism selected from the group consisting of *Thermomyces* genus, *Aspergillus niger, Rhizopus* genus, *Aspergillus oryzae, Penicillium* genus, *Pseudomonas* genus, *Humicola* genus, *Aspergillus melleus* (acylase), *Burkholderia* genus and *Streptomyces* genus.

As the enzyme which gives (S)-N-protected-propargylglycine with an enantiomer excess of over 88% e.e., there are specifically mentioned hydrolysis enzymes derived from a microorganism selected from the group consisting of *Thermomyces lanuginosa, Aspergillus niger, Rhizopus niveus, Aspergillus oryzae, Penicillium citrinum, Pseudomonas* sp., *Humicola* sp. *Aspergillus melleus* (acylase), *Burkholderia cepacia* and *Streptomyces caespitosus*.

On the other hand, as the enzyme giving a (R)-N-protected-propargylglycine ester with an enantiomer excess of over 88% e.e. which is a precursor of (R)-N-protected-propargylglycine, there are mentioned hydrolysis enzymes derived from a microorganism selected from the group consisting of *Thermomyces* genus, *Aspergillus oryzae, Penicillium* genus, *Aspergillus* melleus, *Rhizopus niveus, Humicola* sp., *Candida* genus and *Streptomyces* genus.

On the other hand, as the enzyme which gives a (R)-N-protected-propargylglycine ester with an enantiomer excess of over 88% e.e. which is a precursor of (R)-N-protected-propargylglycine, there are specifically mentioned hydrolysis enzymes derived from a microorganism selected from the group consisting of *Thermomyces lanuginosa, Aspergillus oryzae, Penicillium citrinum, Aspergillus melleus, Rhizopus niveus* (protease), *Humicola* sp., *Candida antactica* and *Streptomyces caespitosus*.

The enzyme which has an ability of asymmetrical hydrolysis for the above-mentioned substrate and has an ability to produce optically active N-protected-propargylglycine may be an enzyme derived from a mutant induced from the above-mentioned microorganism by treatment with a mutagen or ultraviolet ray and the like, an enzyme produced by a recombinant microorganism transformed by introduction of a gene coding this enzyme contained in these microorganisms, or a mutation type enzyme obtained by deletion, addition or substitution of one or more specific amino acids in an amino acid sequence of this enzyme by a gene engineering strategy.

As the method of producing a recombinant microorganism transformed by introduction of a gene coding this enzyme, there are mentioned methods according to usual gene engineering strategies described in, for example, J. Sambrook, E. F. Fritsch, T. Maniatis; Molecular Cloning 2nd edition, Cold Spring Harbor Laboratory (1989).

As the method of producing a mutant enzyme by a gene engineering strategy, for example, a method of Olfert Landt et al. (Gene 96, 125-128, 1990) is mentioned, and specifically, methods according to methods described in Japanese Patent Application Laid-Open (JP-A) Nos. 2000-78988 and 7-213280 are mentioned.

A microorganism producing an enzyme can be liquid-cultured by a usual method. As the medium, various media appropriately containing carbon sources, nitrogen sources, inorganic substances and the like usually used in microorganism culturing can be used.

As the carbon source, for example, glucose, glycerin, organic acids, molasses and the like are mentioned.

As the nitrogen source, for example, peptone, yeast extract, malt extract, soybean powder, corn steep liquor, cotton seed powder, dry yeast, casamino acid, ammonium chloride, ammonium nitrate, ammonium sulfate, urea and the like are mentioned.

As the inorganic substance, for example, hydrochlorides of metals such as potassium, sodium, magnesium, iron, manganese, cobalt, zinc and the like, sulfates of the above-mentioned metals, phosphates of the above-mentioned metals, and the like are mentioned. More specifically mentioned are potassium chloride, sodium chloride, magnesium sulfate, ferrous sulfate, manganese sulfate, cobalt chloride, zinc sulfate, potassium phosphate, sodium phosphate and the like.

For enhancing an ability of asymmetrical hydrolysis of a hydrolysis enzyme in the above-mentioned microorganism, olive oil, triglyceride such as tributyrin and the like, or the above-mentioned substrate may be added to a medium.

It is usually preferable to conduct culturing in an aerobic atmosphere, and shaking culturing or aeration culturing is preferable. The culturing temperature is usually in a range of about 20 to 40%, preferably in a range of 25 to 35° C. The culturing pH is preferably in a range of 6 to 8. The culturing time is preferably in a range of 1 to 7 days though varying depending on conditions.

A solid culturing method can also be adopted providing a microorganism bodies having an ability of asymmetrical hydrolysis of the above-mentioned substrate is obtained.

As a method of purifying the above-mentioned enzyme from a microorganism culture cultured as described above, methods generally adopted in purification of an enzyme can be adopted.

For example, first, microorganism bodies in a microorganism culture is fractured by a method such as ultrasonic treatment, dinomill treatment, French press treatment and the like. Next, insoluble substances are removed from the resultant fracture liquid by centrifugal separation and the like, then, the intended enzyme can be purified by cation exchange column chromatography, anion exchange column chromatography, hydrophobic column chromatography and gel filtration column chromatography and the like used for purification of an enzyme, singly or in appropriate combination of two or more of them As examples of a carrier used in these column chromatography methods, DEAE-Sepharose fastflow (manufactured by Amarsham Farmacia, Biotech), Butyl-Toyopearl650S (manufactured by Tosoh Corp.) and the like are mentioned.

The enzyme can be used in various forms such as purified enzyme, crude enzyme, microorganism cultured substance, microorganism bodies, and treated substances thereof, and the like.

Examples of the above-mentioned treated substances include freeze-dried microorganism bodies, acetone dry microorganism bodies, ground microorganism bodies, auto-digested microorganism bodies, ultrasonic wave-treated microorganism bodies, microorganism bodies extract, alkali-treated microorganism bodies and the like. Further, enzymes of various purities and forms as described above may be immobilized for use by known methods such as a method of adsorption to an inorganic carrier such as silica gel, ceramics and the like, cellulose, ion exchange resin and the like, a polyacrylamide method, a sulfur-containing polysaccharide gel method such as a carrageenan gel method, an alginic acid gel method, an agar gel method and the like.

The use amount of an enzyme is appropriately selected so that the reaction time does not delay and selectivity does not lower.

For example, when a purified enzyme or crude enzyme is used, its use amount is usually in a range of 0.001 to 2-fold by weight, preferably in a range of 0.002 to 0.5-fold by weight based on the above-mentioned substrate.

When a microorganism cultured substance, microorganism bodies or treated substance thereof is used, its use amount is usually in a range of 0.01 to 200-fold by weight, preferably in a range of 0.1 to 50-fold by weight based on the above-mentioned substrate.

As water used in the asymmetric hydrolysis reaction, a buffering aqueous solution is usually used. Examples of the buffering aqueous solution include buffering aqueous solutions of inorganic acid salts such as alkali metal phosphate aqueous solutions such as a sodium phosphate aqueous solution, potassium phosphate aqueous solution and the like, buffering aqueous solutions of organic acid salts such as alkali metal acetates such as a sodium acetate aqueous solution, potassium acetate aqueous solution and the like.

The use amount of water is usually in a range of 0.5 to 200-fold by weight based on the substrate.

The asymmetric hydrolysis reaction in the present invention may be conducted in the presence of an organic solvent such as a hydrophobic organic solvent, hydrophilic organic solvent and the like.

Examples of the hydrophobic organic solvent include aliphatic ethers such as tert-butyl methyl ether, diisopropyl ether and the like; hydrocarbons such as toluene, hexane, cyclohexane, heptane, octane, isooctane and the like.

Examples of the hydrophilic organic solvent include alcohols such as tert-butanol, methanol, ethanol, isopropanol, isobutanol, n-butanol and the like; alicyclic ethers such as tetrahydrofuran and the like; sulfoxides such as dimethyl sulfoxide and the like; ketones such as acetone and the like; nitrites such as acetonitrile and the like; amides such as N,N-dimethylformamide, and the like.

These hydrophobic organic solvents and hydrophilic organic solvents may be used each singly or in admixture of two or more. The hydrophobic organic solvent and hydrophilic organic solvent may be mixed.

When the above-mentioned organic solvents are used, the use amount thereof is usually 200-fold by weight or less, preferably in a range of 0.1 to 100-fold by weight based on the substrate.

The asymmetric hydrolysis reaction is conducted, for example, by a method of mixing water, substrate and enzyme. When the organic solvent is used, this organic solvent, water, substrate and enzyme may be advantageously mixed.

The pH in the asymmetric hydrolysis reaction is usually in a range of 4 to 10, preferably in a range of 6 to 8 though varying depending on the kind of an enzyme. The pH may also be controlled in the above-mentioned range by adding a base during the reaction.

Examples of the above-mentioned base include alkali metal hydroxides such as sodium hydroxide, potassium hydroxide and the like, carbonates of alkali metals such as sodium carbonate, potassium carbonate and the like, carbonates of alkali earth metals such as calcium carbonate and the like, bicarbonates of alkali metals such as sodium hydrogencarbonate, potassium hydrogencarbonate and the like, phosphates such as sodium dihydrogenphosphate, disodium hydrogenphosphate, potassium dihydrogenphosphate, dipotassium hydrogenphosphate and the like, organic bases such as triethylamine, pyridine and the like, ammonia, and the like.

The above-mentioned bases may be used singly or in admixture of two or more. The base is added usually in the form of aqueous solution, however, it may be added in the form of solution of a mixture of an organic solvent and water. As the above-mentioned organic solvent, for example, the same solvents as used in the asymmetric hydrolysis reaction may be used.

The base may be added in the form of solid, and may be added in the form of suspension.

The reaction temperature in the asymmetric hydrolysis is usually in a range of about 5 to 65%, and preferably in a range of about 20 to 50%. It is preferable that the reaction temperature is within the above-mentioned range since then stability of an enzyme can be maintained.

Thus, a reaction solution containing optically active N-protected-propargylglycine of the formula (2) [hereinafter, referred to as carboxylic acid as asymmetric hydrolyzate in some cases] and optically active N-protected-propargylglycine ester remaining without asymmetric hydrolysis [hereinafter, referred to as remaining ester in some cases] is obtained.

For separating these compounds in the reaction solution, or for separating these compounds from enzymes and buffering agents used in the reaction, a post treatment operation may be further conducted.

As the post treatment operation, there are mentioned, for example, a method in which a solvent in the reaction solution is distilled off, then, separation and purification are effected using silica gel chromatography, a method in which separation and purification are effected by a liquid separation operation.

When an organic solvent dissolvable in both water and hydrophobic organic solvent in the reaction is used in effecting separation and purification by a liquid separation operation, this solvent dissolvable in both water and hydrophobic organic solvent may also be removed by distillation before the liquid separation operation.

When an enzyme, immobilized carrier and the like which are insoluble in a solution containing a carboxylic acid as asymmetric hydrolyzate, and a remaining ester are present, these enzyme and immobilized carrier may be removed by filtration.

In the present invention, for separating a carboxylic acid as asymmetric hydrolyzate, and a remaining ester, it may be advantageous that the remaining ester present in the reaction mixture is extracted using a hydrophobic organic solvent, then, the organic layer is separated from an aqueous layer. As the hydrophobic organic solvent used in the above-mentioned extraction, for example, aliphatic ethers such as tert-butyl methyl ether, isopropyl ether and the like; hydrocarbons such as toluene, hexane, cyclohexane, heptane, octane, isooctane and the like; halogenated hydrocarbons such as dichloromethane, dichloroethane, chloroform, chlorobenzene, orthodichlorobenzene and the like; esters such as methyl acetate, ethyl acetate, butyl acetate and the like.

When the above-exemplified hydrophobic organic solvents are used in the asymmetric hydrolysis reaction, a liquid separation operation can also be conducted without any other procedures. When a hydrophobic organic solvent is not used in the asymmetric hydrolysis reaction or when liquid separation is not easy because of small use amount of a hydrophobic organic solvent or water, it may be advantageous that a hydrophobic organic solvent and/or water is appropriately added, then, the mixture is allowed to stand still to cause liquid separation.

Though the use amount of the above-mentioned hydrophobic organic solvent is not particularly restricted, it is usually in a range of 0.1 to 200-fold by weight, preferably in a range of 0.2 to 100-fold by weight based on the substrate.

The pH in the above-mentioned extraction and liquid separation operation is usually in a range of 6 to 12, preferably in a range of 7 to 10.

In separating a remaining ester and a carboxylic acid as asymmetric hydrolyzate, an acid or base can also be used for controlling pH of the liquid in the above-mentioned range.

Examples of the above-mentioned acid include hydrogen chloride, hydrogen bromide, inorganic acids such as sulfuric acid, phosphoric acid and the like, acidic salts of the inorganic acids with metals, organic acids such as acetic acid, citric acid, methanesulfonic acid and the like, and acidic salts of the organic acids with metals, and the like. As the above-mentioned bases, the same bases as used for controlling pH in the reaction can also be used.

When separation of a remaining ester and a carboxylic acid as asymmetric hydrolyzate is insufficient, the above-mentioned extraction and liquid separation operations may be repeated several times.

The remaining ester separated from a carboxylic acid as asymmetric hydrolyzate by the above-mentioned extraction can be isolated by distilling off an organic solvent in an oil phase.

The above-mentioned remaining ester isolated by distilling off an organic solvent in an oil phase may be further purified by column chromatography and the like.

The remaining ester obtained by the above-mentioned operation can be derived into optically active N-protected-propargylglycine, for example, by hydrolysis in the presence of an alkali. This optically active N-protected-propargylglycine may be further purified by column chromatography, recrystallization and the like.

The carboxylic acid as asymmetric hydrolyzate is present in an aqueous layer in the above-mentioned extraction operation. For separating this carboxylic acid present in an aqueous layer from water-soluble components such as an enzyme, buffering agent and the like, it may be advantageous that the carboxylic acid is extracted into an organic layer using a hydrophobic organic solvent, then, the organic layer is separated from an aqueous layer. As the hydrophobic organic solvent used in the above-mentioned extraction, the same solvents as used in the above-mentioned extraction of a remaining ester can be used. The use amount of the hydrophobic organic solvent is usually in a range of about 0.1 to 200-fold by weight, preferably in a range of about 0.2 to 100-fold by weight based on the substrate.

The pH in extraction of the above-mentioned carboxylic acid as asymmetric hydrolyzate is usually in a range of 1 to 7, preferably in a range of 2 to 5.

For controlling liquid property in extraction in the above-mentioned pH range, an acid and a base may also be appropriately used. As such an acid and a base, the same acids and bases as used in the liquid separation operation in separating from the above-mentioned remaining ester can be used.

When the extraction amount of a carboxylic acid as asymmetric hydrolyzate from an aqueous layer is small, the extraction operation and liquid separation operation may be repeated several times.

The carboxylic acid as asymmetric hydrolyzate can be isolated by distilling off a hydrophobic organic solvent in an oil layer obtained in the above-mentioned method. This carboxylic acid may be further purified by column chromatography, recrystallization and the like.

Examples of optically active N-protected-propargylglycine of the formula (2) obtained by the present invention include an optical active N-tert-butoxycarbonyl-propargylglycine, optical active N-benzyloxycarbonyl-propargylglycine, optical active N-p-methoxybenzyloxycarbonyl-propargylglycine, optical active N-p-nitrobenzyloxycarbonyl-propargylglycine, optical active N-allyloxycarbonyl-propargylglycine, optical active N-9-fluorenylmethoxycarbonyl-propargylglycine, optical active N-acetyl-propargylglycine, optical active N-benzyl-propargylglycine, and the like.

According to the method of the present invention, optically active N-protected-propargylglycine of the formula (2) having high optical purity can be produced by using a certain kind of enzyme.

Specifically, according to the method of the present invention, (S)-N-protected-propargylglycine having high optical purity can be obtained. According to another method of the present invention, (R)-N-protected-propargylglycine ester having high optical purity can be obtained. Further, according to the method of the present invention, (R)-N-protected-propargylglycine having high optical purity can be obtained.

EXAMPLES

The present invention will be illustrated further in detail based on the following examples, but it is needless to say that the scope of the invention is not limited to these examples.

Examples 1 to 19

Various enzymes shown in the following Table 1 were weighed in amounts shown in the following Table 2, respectively. Then, into the above-mentioned enzyme was added a solution prepared by dissolving 0.1 ml of a 2 M tert-butyl methyl ether solution of N-tert-butoxycarbonyl-propargylglycine ethyl ester into 5 ml of a 100 mM potassium phosphate buffering solution (pH 7.0). The resultant solution was stirred at 40° C. for 20 hours. Then, 6.4 ml of water and 8.6 ml of acetonitrile were added and mixed. The resultant uniform solution was analyzed by HPLC [column: CHIRALCEL OJ-RH, 4.6 mmϕ×15 cm (manufactured by Daicel Chemical Industries, Ltd.)], and the yields and enantiomer excess of the resultant optically active N-tert-butoxycarbonyl-propargylglycine and N-tert-butoxycarbonyl-propargylglycine ethyl ester were calculated. The results are shown in Table 2.

TABLE 1

| Ex. | Origin of enzyme (enzyme type) | Name of enzyme (enzyme manufacturer) |
|---|---|---|
| 1 | *Thermomyces lanuginosa* (lipase) | Lipase CE "amino" 5 (Amano Enzyme) |
| 2 | *Aspergillus niger* (lipase) | Lipase A "Amano" 6 (Amano Enzyme) |
| 3 | *Rhizopus niveus* (lipase) | Lipase N "Amano" (Amano Enzyme) |
| 4 | *Aspergillus oryzae* (protease) | Protease A "Amano" (Amano Enzyme) |
| 5 | *Penicillium citrinum* (protease) | Protease B "Amano" (Amano Enzyme) |
| 6 | *Aspergillus oryzae* (protease) | Protease M "Amano" (Amano Enzyme) |
| 7 | *Aspergillus melleus* (protease) | Protease P "Amano" (Amano Enzyme) |
| 8 | *Rhizopus niveus* (protease) | Newlase F (Amano Enzyme) |
| 9 | *Pseudomonas* sp. (c. esterase) | CHE "Amano" 2 (Amano Enzyme) |
| 10 | *Humicola* sp. (lipase) | Lipase CE (Amano Enzyme) |
| 11 | *Aspergillus melleus* (acylase) | Acylase (Amano Enzyme) |
| 12 | *Burkholderia cepacia* (lipase) | Chirazyme L-1, lyo (Roche Diagnostics) |
| 13 | *Pseudomonas* sp. (lipase) | Chirazyme L-6, lyo (Roche Diagnostics) |
| 14 | *Candida antactica*, fraction B (lipase) | Chirazyme L-2, c-f., C2, lyo (Roche Diagnostics) |
| 15 | thermophilic microorganism (esterase) | Chirazyme E-3, lyo (Roche Diagnostics) |
| 16 | *Burkholderia cepacia* (lipase) | see JP-A No. 10-210975 |
| 17 | *Streptomyces caespitosus* (protease) | protease |
| 18 | *Bacillus licheniformis* (α-amylase) | Termamyl 120L type L (Novozyme) |
| 19 | *Bacillus subtilis* (α-amylase) | BAN (Novozyme) |

TABLE 2

| | | N-tert-butoxycarbonyl-propargylglycine | | | N-tert-butoxycarbonyl-propargylglycine ethyl ester | | |
|---|---|---|---|---|---|---|---|
| Ex. | Enzyme amount (mg) | Yield (%) | Enantiomer excess (% e.e.) | Excess optical isomer | Yield (%) | Enantiomer excess (% e.e.) | Excess optical isomer |
| 1 | 1.9 | 50 | 97.7 | S-body | 50 | 100.0 | R-body |
| 2 | 1.9 | 40 | 98.3 | S-body | 60 | 67.0 | R-body |
| 3 | 2.0 | 47 | 96.7 | S-body | 53 | 86.2 | R-body |
| 4 | 2.2 | 51 | 94.2 | S-body | 49 | 100.0 | R-body |
| 5 | 2.1 | 51 | 97.0 | S-body | 49 | 100.0 | R-body |
| 6 | 1.9 | 50 | 97.7 | S-body | 50 | 100.0 | R-body |
| 7 | 2.1 | 55 | 84.3 | S-body | 45 | 100.0 | R-body |
| 8 | 1.9 | 49 | 99.2 | S-body | 51 | 96.8 | R-body |
| 9 | 2.0 | 42 | 97.4 | S-body | 58 | 72.4 | R-body |
| 10 | 1.9 | 51 | 97.3 | S-body | 49 | 100.0 | R-body |
| 11 | 2.0 | 52 | 94.3 | S-body | 48 | 100.0 | R-body |
| 12 | 1.9 | 37 | 96.6 | S-body | 63 | 57.2 | R-body |
| 13 | 2.1 | 46 | 96.5 | S-body | 54 | 80.1 | R-body |
| 14 | 10.0 | 59 | 62.4 | S-body | 41 | 100.0 | R-body |
| 15 | 1.9 | 54 | 81.4 | R-body | 46 | 97.3 | S-body |
| 16 | 2.1 | 70 | 97.1 | S-body | 30 | 88.8 | R-body |
| 17 | 2.0 | 50 | 98.4 | S-body | 50 | 100.0 | R-body |
| 18 | 103.7 | 50 | 97.8 | S-body | 50 | 100.0 | R-body |
| 19 | 100.7 | 50 | 99.2 | S-body | 50 | 100.0 | R-body |

Example 20

4.41 g of disodium hydrogenphosphate and 2.48 g of sodium dihydrogenphosphate were dissolved in 518 g of water, to prepare a phosphate buffering solution of pH 7.0. To this phosphate buffering solution was added 0.42 g of Protease B "AMANO" (manufactured by Amano Enzyme) as a protease derived from *Penicillium citrinum* and 25.2 g of a tert-butyl methyl ether solution of racemic N-tert-butoxycarbonyl-propargylglycine ethyl ester (40% solution, net 10 g, 41 mmol) and the mixture was stirred at 40% for 9 hours. After completion of the reaction, 76.7 g of tert-butyl methyl ether was added and the mixture was stirred for 10 minutes. After stirring, an oil layer and an aqueous layer were separated by liquid separation. To the resultant aqueous layer was added 76.7 g of tert-butyl methyl ether, and further, an extraction operation was conducted, then, liquid separation was conducted to separate an oil layer and an aqueous layer. The resultant aqueous layer was concentrated under reduced pressure until the original weight became one-third or less, then, sodium chloride was added until saturated concentration and dissolved. To this aqueous solution was added 93.4 g of ethyl acetate and the mixture was stirred for 10 minutes, then, liquid separation was conducted to separate an oil layer and an aqueous layer. To the resultant aqueous layer was added 93.4 g of ethyl acetate, and further, an extraction operation was conducted, then, liquid separation was effected to separate an oil layer and an aqueous layer. The resultant oil layers were combined, then, dried over sodium sulfate. Then, the solvent was distilled off, to obtain 4.0 g of colorless solid (S)-N-tert-butoxycarbonyl-propargylglycine.

The yield of (S)-N-tert-butoxycarbonyl-propargylglycine was 45%. The enantiomer excess was 99% e.e. or more.

Example 21

3.97 g of disodium hydrogenphosphate and 2.24 g of sodium dihydrogenphosphate were dissolved in 466 g of water. To the resultant solution was added a 10% sodium hydroxide aqueous solution to prepare a phosphate buffering solution having pH controlled at 7.0. To this phosphate buffering solution was added 0.30 g of Protease B "AMANO" (manufactured by Amano Enzyme) as a protease derived from *Penicillium citrinum* and 15.0 g (62 mmol) of racemic N-tert-butoxycarbonyl-propargylglycine ethyl ester and the mixture was stirred at 40° C. for 7.5 hours. During the reaction, a 5% sodium hydroxide aqueous solution was added at appropriate moment so as to keep pH of the liquid at 7.0. After completion of the reaction, 115 g of tert-butyl methyl ether was added and the mixture was stirred for 10 minutes. After stirring, an oil layer and an aqueous layer were separated by liquid separation. To the resultant aqueous layer was added 115 g of tert-butyl methyl ether, and further, an extraction operation was conducted. Thereafter, liquid separation was conducted to separate an oil layer and an aqueous layer. The resultant aqueous layer was concentrated under reduced pressure until the original weight became one-third or less, then, sodium chloride was added until saturated concentration and dissolved. To this aqueous solution was added 140 g of ethyl acetate and the mixture was stirred for 10 minutes, then, liquid separation was conducted to separate an oil layer and an aqueous layer. To the resultant aqueous layer was added 140 g of ethyl acetate, and further, an extraction operation was conducted, then, liquid separation was effected to separate an oil layer and an aqueous layer. The resultant oil layers were combined, then, dried over magnesium sulfate. After drying, the solvent was distilled off, to obtain 5.7 g of colorless solid (S)-N-tert-butoxycarbonyl-propargylglycine.

The yield of (S)-N-tert-butoxycarbonyl-propargylglycine was 43%, and the enantiomer excess was 99% e.e. or more.

INDUSTRIAL APPLICABILITY

Optically active N-protected-propargylglycine obtained by the present invention is useful as an intermediate compound in producing agricultural chemicals, antibiotics and the like, and specifically, very useful as a synthesis intermediate of a polypeptide having renin inhibiting activity (see, WO 9309086), a synthesis intermediate of a peptide-based compound having HIV protease inhibiting activity (see, JP-A No. 5-170722), a synthesis intermediate of a carboxylic acid derivative having matrix metalloproteinase inhibiting activity expected to be applied to curative medicines of cancer, rheumatoid arthritis (see, J. Med. Chem. 2001, 44, 1060-71), and the like.

What is claimed is:

1. A method for producing (S)—N-protected-propargylglycine of formula (2), wherein the method comprises asymmetrically hydrolyzing an N-protected-propargylglycine ester of formula (1) by an asymmetric hydrolysis enzyme or a cultured substance of a microorganism having an ability of producing said enzyme,

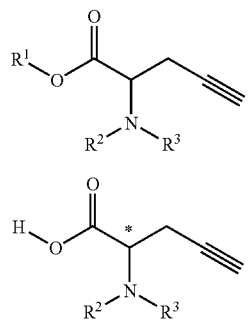

wherein, $R^1$ represents an alkyl group having 1 to 4 carbon atoms, $R^2$ and $R^3$ each independently represent a hydrogen atom or a protective group of an amino group, $R^2$ and $R^3$ being not simultaneously a hydrogen atom, and a carbon atom appended with a mark * represents an asymmetric carbon atom, wherein the asymmetric hydrolysis enzyme is a lipase, protease, acylase, esterase, or α-amylase obtained from a microorganism selected from the group consisting of *Thermomyces* genus, *Aspergillus* genus, *Rhizopus* genus, *Penicillium* genus, *Pseudomonas* genus, *Humicola* genus, *Burkholderia* genus, *Candida* genus, *Bacillus* genus and *Streptomyces* genus.

2. The method according to claim 1, wherein $R^2$ represents a protective group of an amino group of the formula $R^4$—O—CO, wherein R4 represents an alkyl group, aralkyl group, aryl group or a protective group of the formula $R^7$—CH2-, wherein $R^7$ represents an aryl group and $R^3$ represents a hydrogen atom.

3. The method according to claim 1, wherein $R^2$ represents a tert-butoxycarbonyl group and $R^3$ represents a hydrogen atom.

4. The method according to claim 1, wherein $R^1$ represents an ethyl group.

5. The method according to claim 1, wherein the asymmetric hydrolysis enzyme is a hydrolysis enzyme obtained from a microorganism selected from the group consisting of *Thermomyces* genus, *Aspergillus niger*, *Rhizopus* genus, *Aspergillus oryzae*, *Penicillium* genus, *Pseudomonas* genus, *Humicola* genus, *Aspergillus melleus*, *Burkholderia* genus and *Streptomyces* genus.

6. The method according to claim 1, wherein the asymmetric hydrolysis enzyme is a hydrolysis enzyme obtained from a microorganism selected from the group consisting of *Thermomyces lanuginosa*, *Aspergillus niger*, *Rhizopus niveus*, *Aspergillus oryzae*, *Penicillium citrinum*, *Pseudomonas* sp., *Humicola* sp., *Aspergillus melleus*, *Burkholderia cepacia* and *Streptomyces caespltosus*.

7. The production method according to claim 1, wherein the asymmetric hydrolysis enzyme is α-amylase obtained form a microorganism selected from the group consisting of *Bacillus subtilis* and *Bacillus licheniformis*.

8. A method for producing (R)—N-protected-propargylglycine comprising asymmetrically hydrolyzing an (S)—N-protected-propargylglycine ester of an N-protected-propargylglycine ester of the formula (1) by an asymmetric hydrolysis enzyme or a cultured substance of a microorganism having an ability of producing said enzyme, separating (S)—N-protected-propargylglycine and hydrolyzing an unreacted (R)—N-protected-propargylglycine ester

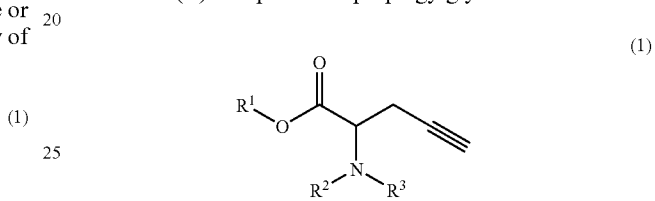

wherein, $R^1$ represents an alkyl group having 1 to 4 carbon atoms, $R^2$ and $R^3$ each independently represent a hydrogen atom or a protective group of an amino group, $R^2$ and $R^3$ being not simultaneously a hydrogen atom, wherein the asymmetric hydrolysis enzyme is a lipase, protease, acylase, esterase or α-amylase obtained from a microorganism selected from the group consisting of *Thermomyces* genus, *Aspergillus* genus, *Rhizopus* genus, *Penicillium* genus, *Pseudomonas* genus, *Humicola* genus, *Burkholderia* genus, *Candida* genus and *Streptomyces* genus.

9. The method according to claim 8, wherein $R^2$ represents a protective group of an amino group of the formula $R^4$—O—CO, wherein $R^4$ represents an alkyl group, aralkyl group, aryl group or a protective group of the formula $R^7$—CH2—, wherein $R^7$ represents an aryl group and $R^3$ represents a hydrogen atom.

10. The method according to claim 8, wherein $R^2$ represents a tert-butoxycarbonyl group and $R^3$ represents a hydrogen atom.

11. The method according to claim 8, wherein $R^1$ represents an ethyl group.

12. The method according to claim 8, wherein the asymmetric hydrolysis enzyme is obtained from a microorganism selected from the group consisting of *Thermomyces* genus, *Aspergillus oryzae*, *Penicillium* genus, *Aspergillus melleus*, *Rhizopus niveus*, *Humicola* sp., *Candida* genus and *Streptomyces* genus.

13. The method according to claim 8, wherein the asymmetric hydrolysis enzyme is obtained from a microorganism selected from the group consisting of *Thermomyces* genus, *Aspergillus oryzae*, *Penicillium* genus, *Aspergillus melleus*, *Rhizopus niveus*, *Humicola* sp., *Candida* genus and *Streptomyces* genus.

14. The method according to claim 8, wherein the asymmetric hydrolysis enzyme is α-amylase obtained form a microorganism selected from the group consisting of *Bacillus subtilis* and *Bacillus licheniformis*.

15. A method for producing (R)—N-protected-propargylglycine comprising asymmetrically hydrolyzing an (S)—

N-protected-propargylglycine ester of a N-protected-propargylglycine ester of formula (1) by an esterase obtained from a thermophillic microorganism, separating (S)—N-protected-propargylglycine, and hydrolyzing an unreacted (R)—N-protected-propargylglycine ester

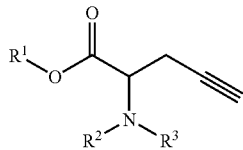

(1)

wherein, $R^1$ represents an alkyl group having 1 to 4 carbon atoms, $R^2$ and $R^3$ each independently represent a hydrogen atom or a protective group of an amino group, $R^2$ and $R^3$ being not simultaneously a hydrogen atom.

16. The method according to claim 1, wherein the asymmetric hydrolysis enzyme is a lipase, protease, acylase, esterase, or α-amylase obtained from a microorganism selected from the group consisting of *Thermomyces lanuginosa, Aspergillus niger, Rhizopus niveus, Aspergillus oryzae, Penicillium citrinum, Pseudomonas* sp., *Humicola* sp., *Aspergillus melleus, Burkholderia cepacia, Streptomyces caespitosus, Bacillus licheniformis,* and *Bacillus subtilis.*

* * * * *